US008012160B2

(12) United States Patent
Jensen et al.

(10) Patent No.: US 8,012,160 B2
(45) Date of Patent: *Sep. 6, 2011

(54) SYSTEM AND METHOD FOR RELEASABLY HOLDING A SURGICAL INSTRUMENT

(75) Inventors: Joel F. Jensen, Redwood City, CA (US); Philip S. Green, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 1071 days.

This patent is subject to a terminal disclaimer.

(21) Appl. No.: 11/522,576

(22) Filed: Sep. 18, 2006

(65) Prior Publication Data
US 2007/0021776 A1 Jan. 25, 2007

Related U.S. Application Data

(60) Continuation of application No. 10/265,285, filed on Oct. 4, 2002, now Pat. No. 7,204,844, which is a continuation of application No. 09/521,253, filed on Mar. 8, 2000, now Pat. No. 6,461,372, which is a division of application No. 09/105,706, filed on Jun. 26, 1998, now Pat. No. 6,080,181, which is a division of application No. 08/848,934, filed on May 1, 1997, now Pat. No. 5,810,880, which is a division of application No. 08/485,587, filed on Jun. 7, 1995, now Pat. No. 5,649,956.

(51) Int. Cl.
*A61B 19/00* (2006.01)
(52) U.S. Cl. ....................................... 606/130
(58) Field of Classification Search .................. 606/130, 606/131, 205–211, 170, 174, 180; 901/18, 901/21, 23; 414/1, 4, 729
See application file for complete search history.

(56) References Cited

U.S. PATENT DOCUMENTS
1,418,184 A 5/1922 Trunick
(Continued)

FOREIGN PATENT DOCUMENTS
CH 482439 12/1969
(Continued)

OTHER PUBLICATIONS

Vertut, Jean and Coeffet, Philippe Coiffet; " Robot Technology; vol. 3A Teleoperation and Robotics Evolution and Development"; 1986; Prentice-Hall, Inc; Englewood Cliffs, N.J.
(Continued)

*Primary Examiner* — Kevin T Troung

(57) ABSTRACT

The invention is directed to a system and method for releasably holding a surgical instrument (14), such as an endoscopic instrument configured for delivery through a small percutaneous penetration in a patient. The instrument comprises an elongate shaft (100) with a pair of mounting pins (116) laterally extending from the shaft between its proximal and distal ends. An instrument holder comprises a support having a central bore (202) and an axially extending slot (204) for receiving the instrument shaft and the mounting pins. A pair of locking slots (206) are cut into the support transversely to and in communication with the axial slot so that the mounting pins can be rotated within the locking slots. The instrument support further includes a latch assembly for automatically locking the mounting pins within the locking slots to releasably couple the instrument to the instrument holder. With this twist-lock motion, the surgeon can rapidly engage and disengage various instruments from the holder during a surgical procedure, such as open surgery, laparoscopy or thoracoscopy.

14 Claims, 10 Drawing Sheets

U.S. PATENT DOCUMENTS

| | | |
|---|---|---|
| 1,664,210 A | 3/1928 | Hall |
| 2,815,697 A | 12/1957 | Saunders-Singer |
| 2,901,258 A | 8/1959 | Brandafi |
| 3,145,333 A * | 8/1964 | Pardini et al. ................. 318/475 |
| 3,171,549 A | 3/1965 | Orloff |
| 3,463,329 A | 8/1969 | Gartner |
| 3,818,125 A | 6/1974 | Butterfield |
| 3,921,445 A | 11/1975 | Hill et al. |
| 3,923,166 A | 12/1975 | Fletcher et al. |
| 3,934,201 A | 1/1976 | Majefski |
| 4,058,001 A | 11/1977 | Waxman |
| 4,113,115 A | 9/1978 | Yoshio |
| 4,150,326 A | 4/1979 | Engelberger et al. |
| 4,221,997 A | 9/1980 | Flemming |
| 4,260,319 A | 4/1981 | Motoda et al. |
| 4,264,266 A | 4/1981 | Trechsel |
| 4,349,837 A | 9/1982 | Hinds |
| 4,367,998 A | 1/1983 | Causer |
| 4,419,041 A | 12/1983 | Rose |
| 4,436,684 A | 3/1984 | White |
| 4,456,961 A | 6/1984 | Price et al. |
| 4,474,174 A | 10/1984 | Petruzzi |
| 4,490,022 A | 12/1984 | Reynolds |
| 4,503,854 A | 3/1985 | Jako |
| 4,506,393 A | 3/1985 | Murphy |
| 4,510,574 A | 4/1985 | Guittet et al. |
| 4,517,963 A | 5/1985 | Michel |
| 4,562,463 A | 12/1985 | Lipton |
| 4,563,567 A | 1/1986 | Geffroy et al. |
| 4,582,067 A | 4/1986 | Silverstein et al. |
| 4,583,117 A | 4/1986 | Lipton et al. |
| 4,601,000 A | 7/1986 | Montabert |
| 4,636,138 A | 1/1987 | Gorman |
| 4,638,799 A | 1/1987 | Moore |
| 4,651,201 A | 3/1987 | Schoolman |
| 4,655,257 A | 4/1987 | Iwashita |
| 4,672,963 A | 6/1987 | Barken |
| 4,676,243 A | 6/1987 | Clayman |
| 4,722,056 A | 1/1988 | Roberts et al. |
| 4,728,974 A | 3/1988 | Nio et al. |
| 4,744,363 A | 5/1988 | Hasson |
| 4,750,475 A | 6/1988 | Yoshihashi |
| 4,750,487 A | 6/1988 | Zanetti |
| 4,751,925 A | 6/1988 | Tontarra |
| 4,762,455 A | 8/1988 | Coughlan et al. |
| 4,764,944 A | 8/1988 | Finlayson |
| 4,788,482 A | 11/1988 | Tachibana et al. |
| 4,791,588 A | 12/1988 | Onda et al. |
| 4,791,934 A | 12/1988 | Brunnett |
| 4,794,912 A | 1/1989 | Lia |
| 4,806,066 A | 2/1989 | Rhodes et al. |
| 4,808,898 A | 2/1989 | Pearson |
| 4,815,006 A | 3/1989 | Andersson et al. |
| 4,826,392 A | 5/1989 | Hayati |
| 4,833,383 A | 5/1989 | Skarr et al. |
| 4,837,703 A | 6/1989 | Kakazu et al. |
| 4,837,734 A | 6/1989 | Ichikawa et al. |
| 4,853,874 A | 8/1989 | Iwamoto et al. |
| 4,854,301 A | 8/1989 | Nakajima |
| 4,855,822 A | 8/1989 | Narendra et al. |
| 4,860,215 A | 8/1989 | Seraji |
| 4,862,873 A | 9/1989 | Yajima et al. |
| 4,863,133 A | 9/1989 | Bonnell |
| 4,873,572 A | 10/1989 | Miyazaki et al. |
| 4,883,400 A | 11/1989 | Kuban et al. |
| 4,899,730 A | 2/1990 | Stennert et al. |
| 4,921,393 A | 5/1990 | Andeen et al. |
| 4,922,338 A | 5/1990 | Arpino |
| 4,930,494 A | 6/1990 | Takehana et al. |
| 4,941,106 A | 7/1990 | Krieger |
| 4,942,539 A | 7/1990 | McGee et al. |
| 4,943,296 A | 7/1990 | Funakubo et al. |
| 4,947,702 A | 8/1990 | Kato |
| 4,954,952 A | 9/1990 | Ubhayakar et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,002,418 A | 3/1991 | McCown et al. |
| 5,020,001 A | 5/1991 | Yamamoto et al. |
| 5,020,933 A | 6/1991 | Salvestro et al. |
| 5,024,236 A | 6/1991 | Shapiro |
| 5,036,463 A | 7/1991 | Abela et al. |
| 5,045,936 A | 9/1991 | Lobb et al. |
| 5,046,022 A | 9/1991 | Conway et al. |
| 5,050,608 A | 9/1991 | Watanabe et al. |
| 5,053,975 A | 10/1991 | Tsuchihashi et al. |
| 5,056,031 A | 10/1991 | Nakano et al. |
| 5,060,532 A | 10/1991 | Barker |
| 5,062,761 A * | 11/1991 | Glachet ........................ 414/729 |
| 5,065,741 A | 11/1991 | Uchiyama et al. |
| 5,077,506 A | 12/1991 | Krause |
| 5,078,140 A | 1/1992 | Kwoh |
| 5,078,142 A | 1/1992 | Siczek et al. |
| 5,086,401 A | 2/1992 | Glassman et al. |
| 5,090,401 A | 2/1992 | Schwieker |
| 5,096,236 A | 3/1992 | Thony |
| 5,097,839 A | 3/1992 | Allen |
| 5,098,426 A | 3/1992 | Sklar et al. |
| 5,125,888 A | 6/1992 | Howard et al. |
| 5,141,519 A | 8/1992 | Smith et al. |
| 5,142,930 A | 9/1992 | Allen et al. |
| 5,145,227 A | 9/1992 | Monford, Jr. |
| 5,154,717 A | 10/1992 | Matsen, III et al. |
| 5,170,347 A | 12/1992 | Tuy et al. |
| 5,182,641 A | 1/1993 | Diner et al. |
| 5,184,601 A | 2/1993 | Putman |
| 5,187,574 A | 2/1993 | Kosemura et al. |
| 5,187,796 A | 2/1993 | Wang et al. |
| 5,188,111 A | 2/1993 | Yates et al. |
| 5,201,325 A | 4/1993 | McEwen et al. |
| 5,201,743 A | 4/1993 | Haber et al. |
| 5,209,747 A | 5/1993 | Knoepfler |
| 5,216,596 A | 6/1993 | Weinstein |
| 5,217,003 A | 6/1993 | Wilk |
| 5,219,351 A | 6/1993 | Teubner et al. |
| 5,221,283 A | 6/1993 | Chang |
| 5,222,499 A | 6/1993 | Allen et al. |
| 5,228,429 A | 7/1993 | Hatano |
| 5,230,338 A | 7/1993 | Allen et al. |
| 5,235,510 A | 8/1993 | Yamada et al. |
| 5,236,432 A | 8/1993 | Matsen, III et al. |
| 5,240,011 A | 8/1993 | Assa |
| 5,251,127 A | 10/1993 | Raab |
| 5,253,706 A | 10/1993 | Reid |
| 5,257,203 A | 10/1993 | Riley et al. |
| 5,257,998 A | 11/1993 | Ota et al. |
| 5,260,319 A | 11/1993 | Effland et al. |
| 5,261,404 A | 11/1993 | Mick et al. |
| 5,264,266 A | 11/1993 | Yokoyama et al. |
| 5,271,384 A | 12/1993 | McEwen et al. |
| 5,273,039 A | 12/1993 | Fujiwara et al. |
| 5,273,309 A | 12/1993 | Lau et al. |
| 5,279,309 A | 1/1994 | Taylor et al. |
| 5,280,427 A | 1/1994 | Magnusson et al. |
| 5,281,220 A | 1/1994 | Blake, III |
| 5,282,606 A | 2/1994 | Praiss |
| 5,284,130 A | 2/1994 | Ratliff |
| 5,289,273 A | 2/1994 | Lang |
| 5,299,288 A | 3/1994 | Glassman et al. |
| 5,313,306 A | 5/1994 | Kuban et al. |
| 5,325,866 A | 7/1994 | Krzyzanowski |
| 5,339,799 A | 8/1994 | Kami et al. |
| 5,343,391 A | 8/1994 | Mushabac |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,377,310 A | 12/1994 | Jain et al. |
| 5,377,683 A | 1/1995 | Barken |
| 5,382,885 A | 1/1995 | Salcudean et al. |
| 5,396,685 A | 3/1995 | Wilk |
| 5,397,323 A | 3/1995 | Taylor et al. |
| 5,398,685 A | 3/1995 | Wilk et al. |
| 5,402,801 A | 4/1995 | Taylor |
| 5,417,210 A | 5/1995 | Funda et al. |

| | | | |
|---|---|---|---|
| 5,425,528 A | 6/1995 | Rains et al. |
| 5,441,505 A | 8/1995 | Nakamura |
| 5,445,166 A | 8/1995 | Taylor |
| 5,452,733 A | 9/1995 | Sterman et al. |
| 5,458,574 A | 10/1995 | Machold et al. |
| 5,474,566 A | 12/1995 | Alesi et al. |
| 5,480,409 A | 1/1996 | Riza |
| 5,515,478 A | 5/1996 | Wang |
| 5,524,180 A | 6/1996 | Wang et al. |
| 5,553,198 A | 9/1996 | Wang et al. |
| 5,571,110 A | 11/1996 | Matsen, III et al. |
| 5,572,999 A | 11/1996 | Funda et al. |
| 5,619,992 A | 4/1997 | Guthrie et al. |
| 5,629,594 A | 5/1997 | Jacobus et al. |
| 5,630,431 A | 5/1997 | Taylor |
| 5,631,973 A | 5/1997 | Green |
| 5,636,138 A | 6/1997 | Gilbert et al. |
| 5,645,520 A | 7/1997 | Nakamura et al. |
| 5,649,956 A | 7/1997 | Jensen et al. |
| 5,657,429 A | 8/1997 | Wang et al. |
| 5,735,290 A | 4/1998 | Sterman et al. |
| 5,754,741 A | 5/1998 | Wang et al. |
| 5,762,458 A | 6/1998 | Wang et al. |
| 5,779,623 A | 7/1998 | Bonnell |
| 5,807,378 A | 9/1998 | Jensen et al. |
| 5,808,665 A | 9/1998 | Green |
| 5,810,686 A | 9/1998 | De Jong et al. |
| 5,815,640 A | 9/1998 | Wang et al. |
| 5,817,084 A | 10/1998 | Jensen |
| 5,841,950 A | 11/1998 | Wang et al. |
| 5,855,583 A | 1/1999 | Wang et al. |
| 5,876,325 A | 3/1999 | Mizuno et al. |
| 5,878,193 A | 3/1999 | Wang et al. |
| 5,907,664 A | 5/1999 | Wang et al. |
| 5,911,036 A | 6/1999 | Wright et al. |
| 5,931,832 A | 8/1999 | Jensen |
| 5,954,746 A | 9/1999 | Holthaus et al. |
| 5,971,976 A | 10/1999 | Wang et al. |
| 6,001,108 A | 12/1999 | Wang et al. |
| 6,017,358 A | 1/2000 | Yoon et al. |
| 6,042,599 A | 3/2000 | Huttner et al. |
| 6,063,095 A | 5/2000 | Wang et al. |
| 6,080,181 A | 6/2000 | Jensen et al. |
| 6,461,372 B1 | 10/2002 | Jensen et al. |
| 6,889,116 B2 | 5/2005 | Jinno |
| 7,204,844 B2 | 4/2007 | Jensen et al. |
| 2001/0031983 A1 | 10/2001 | Brock et al. |
| 2002/0087048 A1 | 7/2002 | Brock et al. |
| 2002/0120252 A1 | 8/2002 | Brock et al. |
| 2002/0143319 A1 | 10/2002 | Brock |
| 2005/0222554 A1 | 10/2005 | Wallace |
| 2005/0283140 A1 | 12/2005 | Jensen et al. |

FOREIGN PATENT DOCUMENTS

| | | |
|---|---|---|
| DE | 2819976 | 11/1979 |
| DE | 3806190 | 9/1988 |
| DE | 9204116 U1 | 8/1992 |
| DE | 4213426 | 10/1992 |
| EP | 239409 | 9/1987 |
| EP | 0291292 | 11/1988 |
| EP | 0595291 | 5/1994 |
| EP | 776738 | 6/1997 |
| FR | 2460762 | 1/1981 |
| FR | 2593106 | 3/1990 |
| GB | 0494943 | 10/1938 |
| GB | 2040134 | 8/1980 |
| GB | 2117732 | 10/1983 |
| JP | 59146770 | 8/1984 |
| JP | 2015349 | 1/1990 |
| JP | 6229198 | 8/1994 |
| JP | 7059788 A2 | 3/1995 |
| JP | 7136173 A2 | 5/1995 |
| JP | 2003-61969 | 3/2003 |
| WO | WO 9104711 | 4/1991 |
| WO | WO 9216141 | 10/1992 |
| WO | WO 9313916 | 7/1993 |
| WO | WO 9403113 | 2/1994 |
| WO | WO 9418881 | 9/1994 |
| WO | WO 9426167 | 11/1994 |
| WO | WO 9501757 | 1/1995 |
| WO | WO 9503001 A1 | 2/1995 |

OTHER PUBLICATIONS

"Abstracts and Video Catalogue, 3.sup.rd World Congress of Endoscopic Surgery Abstracts, Surgical Laporoscopy & Endoscopy, vol. 3, No. 3, (1993) pp. 248-275."

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1973, pp. 121-136, vol. 2, Springer-Verlag.

Altamuro, Vincent M., "Automatic Guided Vehicles and Robots," Mark's Standard Handbook for Mechanical Engineers, Ninth Edition, 1987, pp. 4, McGraw-Hill Book Company.

Asada Haruhiko et al., "Development of a direct drive arm using high torque brushless motors," Proc. of 1st Int. Symp. on Robotics Research, 1984, pp. 583-599, Chapter 7, MIT Press.

Askew, Scott R. et al., "Ground control testbed for space station freedom robot manipulators," IEEE Virtual Reality Annual International Symposium, 1993, pp. 69-75, IEEE.

Bejczy, Antal K. et al., "Controlling Remote Manipulators through Kinesthetic Coupling," Computers in Mechanical Engineering, 1983, pp. 48-60, vol. 1-Issue 1.

Ben Gayed et al.,"An Advanced Control Micromanipulator for Surgical Applications," Systems Science, 1987, pp. 123-134, vol. 13.

Bergamasco, Massimo et al., "Advanced Interfaces for Teleoperated Biomedical Robots," IEEE Engineering in Medicine & Biology Society 11.sup.th Annual International Conference, Nov. 9-12, 1989, pp. 912-913, vol. 3, IEEE.

Besant, Colin et al., Abstract of presentation "Camera Control for Laparoscopic Surgery by Speech recognizing Robot: Constant Attention and Better Use of Personnel," 3rd World Congress of Endoscopic surgery, 1993, p. 271, vol. 3-issue 3.

Blue Cross, Another Pair of Hands for Surgeon, The Blue Cross magazine Perspective, 1972, 3 Pages Total.

Bose, Bijo et al., "Tremor compensation for robotics assisted microsurgery," Annual Intl Conf. of IEEE Engineering in Medicine and Biology Society, Oct.-Nov. 1992, pp. 1067-1068, vol. 14—Issue 3, IEEE.

Bowersox, Jon C. et al., "Vascular applications of telepresence surgery: Initial feasibility studies in swine," J. Vascular Surgery, Feb 1996, pp. 281-287, vol. 23—Issue 2.

Charles, Steve et al., "Design of a Surgeon Machine Interface for Teleoperated Microsurgery," Proceedings of IEEE Annual Conference on Engineering in Medicine and Biology, 1989, pp. 0883-0884, vol. 11, IEEE.

Clement, J. et al., "An overview of CAT control in nuclear services," Proceedings, 1985 IEEE International Conference on Robotics and Automation, Mar. 1985, pp. 713-718, vol. 2, IEEE.

Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.

Corcoran, Elizabeth, "Robots for the Operating Room," The New York Times, 2 pages total, Jul. 19 1992, Section 3 p. 9C.

Das, Hari et al., "Kinematic Control and Visual Display of Redundant Teleoperators," IEEE International Conference on Systems, Man, and Cybernetics, 1989, pp. 1072-1077, vol. 3, IEEE.

Davies, Brain L. et al., "A Surgeon Robot for Prostatectomies," Fifth International conference on Advanced Robotics, 1995, pp. 871-875, vol. 1, IEEE.

Dolan J.M. et al., "A Robot in an Operating Room: A Bull in a China Shop," 1987, pp. 1096-1097, vol. 2.

Finlay, Patrick A. et al., "Controlling the movement of a surgical laparoscope," Engineering in Medicine and Biology Magazine, May/Jun. 1995, pp. 289 291, vol. 14-Issue 3, IEEE.

Finlay, Patrick A., "Results of a Feasibility Study Into Applications for Advanced Medical Robots," Joint Coordinating Forum for the International Advanced Robotics Programme, Ottawa Ontario, Canada, Jun. 23-24, 1998, pp. 2.1-2.6.

Fisher Scott S. et al., "Telepresence Master Glove Controller for dexterous robotics end effectors," intelligent Robots and Computer Vision: Fifth in a Series, 1986, pp. 396-401, vol. 725, SPIE.

Fisher, Scott S., "Virtual interface environment," IEEE/A1AA 7th Digital Avionics Systems Conference Ft. Worth TeXas, 1986, pp. 346-350,IEEE.

Flatau, Carl R., "Compact Servo Master-Slave Manipulator With Optimized Communication Links," From 17th Conference on Remote Systems Technology, San Francisco, Calif., 1969, pp. 154-164.

Fu, K.S. et al., "Robotics: control, sensing, vision, and intelligence," 1987, pp. 12-265, Ch. 2 & 5, McGraw-Hill Book Company.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Galloway, Robert L. et al., "A new device for interactive image guided surgery," Proceedings The International Society of Optical Engineering SPIE Medical Imaging V: Image Capture Formatting and Display Kim Y Ed, 1991, pp. 9-18, vol. 1444, SPIE.

Giauser, D. et al., "Conception of a robot dedicated to neurosurgical operations," Fifth International Conference on Advanced Robotics, 1991. Robots in Unstructured Environments, 91 ICAR, 1991, pp. 898-907, vol. 1, IEEE.

Green, Phil, Transcript of "Videotape: Telepresence: Advanced Technology for Enhanced Minimally Invasive Surgery," 1992.

Green, Philip S. et al., Abstract of a presentation "Telepresence: Advanced Teleoperator Technology for Minimally Invasive Surgery," given at the 3rd World Congress of Endoscopic Surgery in Bordeaux, Jun. 18-20, 1992, 2 pages total.

Green, Philip S. et al., Statutory Declaration by Dr. Phillip S. Green, the presenter of the video entitled "Telepresence Surgery: The Future of Minimally Invasive Medicine," European Patent Convention in the Matter of EP-B-653922. 32 pages, Sep. 12, 2000.

Green, Philip S. et al., "Telepresence Surgery," IEEE Engineering in Medicine and Biology Magazine, May/Jun. 1995, pp. 324-329, vol. 14—Issue 3, IEEE.

Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.

Guinot J.C et al., "Analysis of a robot wrist device for mechanical decoupling of end-effector position and orientation," Proceedings of the 6th CISM-IFtoMM Symposium on Theory and Practice of Robots and Manipulators, 1986, pp. 42-53.

Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.

Hayati, S. et al., "Remote Surface Inspection System," Robototics and Autonomous Systems, 1993, pp. 45-59, vol. 11—No. 1, Elsevier Science Publishers.

Held, Richard et al., "Telepresence, Time Delay and Adaptation", *, Spatial Displays and Spatial Instruments Proceedings of a Conference sponsored by NASA Ames Research Center and the School of Optometry, Univ. of California, Aug. 31-Sep. 3, 1987, Published 1989, pp. 28-1 through 28-16.

Hill, John W., "Telepresence surgery demonstration system," Robotics and Automation, 1994, pp. 2302-2307, vol. 3, SRI International.

Holler, Elmar et al., "An ATM based local communication system for telesurgery," Interactive Tech. and New Paradigm Healthcare, 1995, pp. 137-146.

Hunter, Ian, W. et al., "Manipulation and dynamic mechanical testing of microscopic objects using a tele-micro-robot system," IEEE Control Systems Magazine, 1990, pp. 3-9, vol. 10—Issue 2, IEEE.

Hunter, Ian W. et al., "Ophthalmic microsurgical robot and associated virtual environment," Comput. Biol. Med, 1995, vol. 25, Issue 2, pp. 173-182, Pergamon.

Huntert, Ian W. et al., "Manipulation and dynamic mechanical testing of microscopic objects using a tele-micro-robot system," IEEE International Conference onRobotics and Automation, 1989, pp. 1553-1558, IEEE.

Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.

Inoue, Masao; "Six-Axis bilateral control of an articulated slave manipulator using a Cartesian master manipulator," Advanced robotics, 1990, pp. 139-150, vol. 4-Issue 2, Robotic society of Japan.

"Introduction to New Project for The National Research Development Program (Large-Scale Project) in FY 1991—Micromachine Technology", Agency of Industrial Science and Technology Ministry of International Trade and Industry, Japan, 1991, pp. 1-11.

Intuitive Surgical, The da VinciTM Endoscopic Instrument Control System User Manual, 1999, 84 pages.

Jau, B. M., "Anthropomorphic Remote Manipulator," NASA Tech Briefs, Apr. 1991, pp. 92, NASA's Jet Propulsion Laboratory, Pasadena, California.

Kavoussi, Louis R. et al., Telerobotic Assisted Laparoscopic Surgery: Initial Laboratory and Clinical Experience, Urology, Jul. 1994, pp. 15-19, vol. 44—Issue 1.

Kazerooni H., "Design and analysis of the statically balanced direct-drive robot manipulator," Robotics and Computer-Integrated Manufacturing, 1989, pp. 287-293, vol. 6, Issue 4.

Kazerooni, H. et al., "The Dynamics and Control of a Haptic Interface Device," IEEE Transactions on Robotics and Automation, 1994, pp. 453-464, vol. 10—Issue 4, IEEE.

Kazerooni, H., "Human/Robot Interaction via the Transfer of Power and Information Signals Part I: Dynamics and Control Analysis," IEEE International Conference on Robotics and Automation, 1989, pp. 1632-1640, IEEE.

Kazerooni, H, "Human/Robot Interaction via the Transfer of Power and Information Signals—Part II," An Experimental Analysis, Proc. of the 1989 IEEE International Conference on Robotics and Automation, 1989, pp. 1641-1647, vol. 3, IEEE.

Kim, Won S. et al., "A Helmet Mounted Display for Telerobotics," Compcon Spring '88. Thirty-Third IEEE Computer Society International Conference, 1988, pp. 543-547, IEEE.

Krishnan, S.M. et al., Abstract of a presentation "Design Considerations of a New Generation Endoscope Using Robotics and Computer Vision Technology," given at the 3rd World Congress of Endoscopic Surgery in Bordeaux, Jun. 18-20 1992, (1 page total).

Lavallee, Stephane, "A New System for Computer Assisted Neurosurgery," IEEE Eng. in Med. & Biol. Soc. 11th Annual International Conference, Jun. 1989, pp. 926-927, vol. 11.

Mair, Gordon M., Industrial Robotics, Prentice Hall, 1988, pp. 41-43, 49-50, 54, 203-209.

Majima S. et al., "On a Micro Manipulator for Medical Application Stability Consideration of its Bilateral Controller Mechatronics," 1991, pp. 293-309, vol. 1—Issue 3.

Matsushima, K. et al., "Servo Micro-Manipulator Tiny-Micro Mark-1," 4th Symposium on Theory and Practice of Robots and Manipulators, 1982, pp. 193-201.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.

Preising, B. et al., "A Literature Review: Robots in Medicine," IEEE Engineering in Medicine and Biology, 1991, pp. 13-22, 71, vol. 10—Issue 2, IEEE.

Rasor, Ned S. et al., "Endocorporeal Surgery Using Remote Manipulators," Proceedings of the First National Conference held at California Institute of Technology, 1973, pp. 483-492.

Richter, Rutann, "Telesurgery may bridge future gaps," Times Tribune, Jan. 24, 1988, pp. A-1 and A-16.

Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.

Sato, Yoshinobu et al., "The Safety Assessment of Human-Robot Systems(Architectonic principles of hazard-control systems)," JSME International Journal, 1989, pp. 67-74, vol. 32—Issue 1.

Spain, Edward H., "Stereo Advantage for a Peg in Hole Task Using a Force Feedback Manipulator," SPIE Stereoscopic Displays and Applications, 1990, pp. 244-254, vol. 1256, IEEE.

Tachi, Susumu et al., "Tele-Existence Master Slave System for Remote Manipulation (II)," IEEE Conference on Decision and Control Honolulu Hawaii, Dec. 5-7 1990, pp. 85-90, vol. 1—Issue 6, IEEE.

Taubes, Gary et al., "Surgery in Cyberspace," Discover magazine, Dec. 1994, vol. 15, issue 12, pp. 85-92.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.

Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.

Tejima, Noriyuki et al., "A New Microsurgical Robot System for Corneal Transplantation," Precision Machinery, 1988, pp. 1-9, vol. 2, Gordon and Breach Science Publishers Inc.

Tendick, Frank et al., "Analysis of the Surgeon's Grasp for Telerobotic Surgical Manipulation," IEEE 11th Annual Int Conf on Engineering in Medicine and Biology, Jun. 1989, pp. 914-915, IEEE.

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited.

Trevelyan, James P. et al., "Motion Control for a Sheep Shearing Robot," IEEE Robotics Research Conference, the 1st International Symposium, Carroll, NH, USA., 1983, pp. 175-190, MIT Press.

Trevelyan, James P., "Skills for a Shearing Robot: Dexterity and Sensing," Proceedings of Second International Symposium on Robotics Research, 1985, pp. 273-280, Chapter 5, MIT Press.

Trivedi Mohan M. et al., "Developing telerobotic systems using virtual reality concepts," 1993 IEEE/RSJ International Conference on Intelligent Robots and systems, 1993, pp. 352-359, vol. 1, IEEE.

Vertut, Jean et al., "Sensor-aided and/or Computer-aided Bilateral Teleoperator System (SCATS)," Fifth CISM-IFToMM Symposium Theory and Practice of Robots and Manipulators Proceedings of RoManSy '84 part 4, 1985, pp. 281-292, MIT Press.

Vibet, C., "Properties of Master Slave Robots," Motor-con, 1987, pp. 309-316.

* cited by examiner

SYSTEM AND METHOD FOR RELEASABLY HOLDING A SURGICAL INSTRUMENT

This application is a continuation of U.S. application Ser. No. 11/195,494 filed Aug. 1, 2005, which is a continuation of U.S. application Ser. No. 10/265,285 filed Oct. 4, 2002, which is a continuation of U.S. application Ser. No. 09/521,253 filed on Mar. 8, 2000, now U.S. Pat. No. 6,461,372, which is a continuation of U.S. application Ser. No. 09/105,706 filed on Jun. 26, 1998, now U.S. Pat. No. 6,080,181, which is a division of U.S. application Ser. No. 08/848,934, filed on May 1, 1997, now U.S. Pat. No. 5,810,880, which is a division of application Ser. No. 08/485,587, filed on Jun. 7, 1995, now U.S. Pat. No. 5,649,956, all of which are incorporated herein by reference.

This invention was made with Government support under contract awarded by the National Institute for Health (NIH) under grant number 5 R01GM-44902-02. The Government has certain rights in this invention.

BACKGROUND OF THE INVENTION

This invention relates to surgical manipulators and more particularly to robotic assisted apparatus for use in surgery.

In standard laparoscopic surgery, a patient's abdomen is insufflated with gas, and trocar sleeves are passed through small (approximately ½ inch) incisions to provide entry ports for laparoscopic surgical instruments. The laparoscopic surgical instruments generally include a laparoscopes for viewing the surgical field, and working tools such as clamps, graspers, scissors, staplers, and needle holders. The working tools are similar to those used in conventional (open) surgery, except that the working end of each tool is separated from its handle by an approximately 12 inch long extension tube. To perform surgical procedures, the surgeon passes instruments through the trocar sleeves and manipulates them inside the abdomen by sliding them in and out through the sleeves, rotating them in the sleeves, levering (e.g., pivoting) the sleeves in the abdominal wall, and actuating end effectors on the distal end of the instruments.

In robotically-assisted and telerobotic surgery (both open surgery and endoscopic procedures), the position of the surgical instruments is controlled by servo motors rather than directly by hand or with fixed clamps. The servo motors follow the motions of a surgeon's hands as he/she manipulates input control devices at a location that may be remote from the patient. Position, force, and tactile feedback sensors may be employed to transmit position, force, and tactile sensations from the surgical instrument back to the surgeon's hands as he/she operates the telerobotic system.

The servo motors are typically part of an electromechanical device that supports and controls the surgical instruments that have been introduced directly into an open surgical site or through trocar sleeves into the patient's abdomen becomes a body cavity. During the operation, the electromechanical device or instrument holder provides mechanical actuation and control of a variety of surgical instruments, such as tissue graspers, needle drivers, etc, that each perform various functions for the surgeon, i.e., holding or driving a needle, grasping a blood vessel or dissecting tissue.

This new method of performing telesurgery through remote manipulation will create many new challenges. One such challenge is that different surgical instruments will be attached and detached from the same instrument holder a number of times during an operation. In laparoscopic procedures, for example, the number of entry ports into the patient's abdomen is generally limited during the operation because of space constraints as well as a desire to avoid unnecessary incisions in the patient. Thus, a number of different surgical instruments will typically be introduced through the same trocar sleeve during the operation. Likewise, in open surgery, there is typically not enough room around the surgical site to position more than one or two surgical manipulators, and so the surgeon's assistant will be compelled to frequently remove instruments from the holder and exchange them with other surgical tools.

What is needed, therefore, is an improved system and method for releasably coupling a surgical instrument to an instrument holder. The system should be configured to quickly and easily engage and disengage the instrument from the holder to minimize the instrument exchange time during endoscopic surgery. Preferably, the system is part of an electromechanical device that can be coupled to a controller mechanism to form a telerobotic system for operating the surgical instrument by remote control.

BRIEF SUMMARY OF THE INVENTION

According to the invention, a system and method provide for releasably holding a surgical instrument during conventional open surgery or endoscopic procedures, such as laparoscopy. The instrument comprises an elongate shaft with proximal and distal ends and a mounting means having a protrusion extending radially from the shaft between the proximal and distal ends. An instrument holder comprises a support having a body with an axial passage for receiving the instrument shaft and a first hole in communication with the axial passage for receiving the protrusion. A second hole is cut into the body transversely to and in communication with the first hole so that the protrusion can be rotated within the second hole. To prevent the instrument from being accidently twisted and thereby disengaged from the instrument holder during surgery, the holder further includes a locking means coupled to the body for automatically locking the protrusion within the second hole thereby releasably locking the instrument to the instrument holder.

In a preferred configuration, the protrusion of the mounting means comprises a pair of opposing arms, such as mounting pins, extending outward from the instrument shaft. The first hole is an axially extending slot for receiving the mounting pins and the second hole is a perpendicular locking slot having a first portion aligned with the axial slot and a second portion extending circumferentially around the body of the instrument support. With this configuration, the mounting pins can be slid through the axial slot and rotated into the locking slot to attach the instrument to the holder. The instrument can be removed by performing the same two steps in reverse order. With this twist-lock motion, the surgeon can rapidly engage and disengage various instruments from the instrument holder during a surgical procedure.

The locking means preferably comprises a releasable latch assembly for locking the mounting pins to the instrument holder. The latch assembly includes a spring-loaded plunger coupled to a latch that normally locks the instrument in place by capturing the mounting pin in the locking slot. The plunger has a button extending outward from the instrument holder for moving the latch away from the locking slot. The button can be depressed manually or automatically to release the mounting pins and allow instrument exchange when the instrument is easily accessible to the surgeon.

The invention is particularly useful for releasably holding an endoscopic instrument configured for introduction through a small percutaneous penetration into a body cavity, e.g., the abdominal or thoracic cavity. To that end, the instrument preferably includes an end effector, such as a pair of jaws, coupled to the distal end for engaging a tissue structure within the body cavity. To actuate the end effector, the instrument has a second pair of arms, such as actuator pins, laterally extending from the shaft and operatively coupled to the end effector. Preferably, the actuator pins are axially displaceable with respect to the shaft to actuate the end effector (e.g., open and close the jaws). The instrument holder further includes an actuator driver releasably coupled to the actuator arms and to an external driver for actuating the end effector. The actuator driver preferably includes a twist-lock interface having transverse slots similar to that described for the instrument support so that-the instrument can be simultaneously engaged or disengaged from both the instrument support and the actuator driver.

Other features and advantages of the invention will appear from the following description in which the preferred embodiment has been set forth in detail in conjunction with the accompanying drawings.

DETAILED DESCRIPTION OF THE INVENTION

Figure 1:
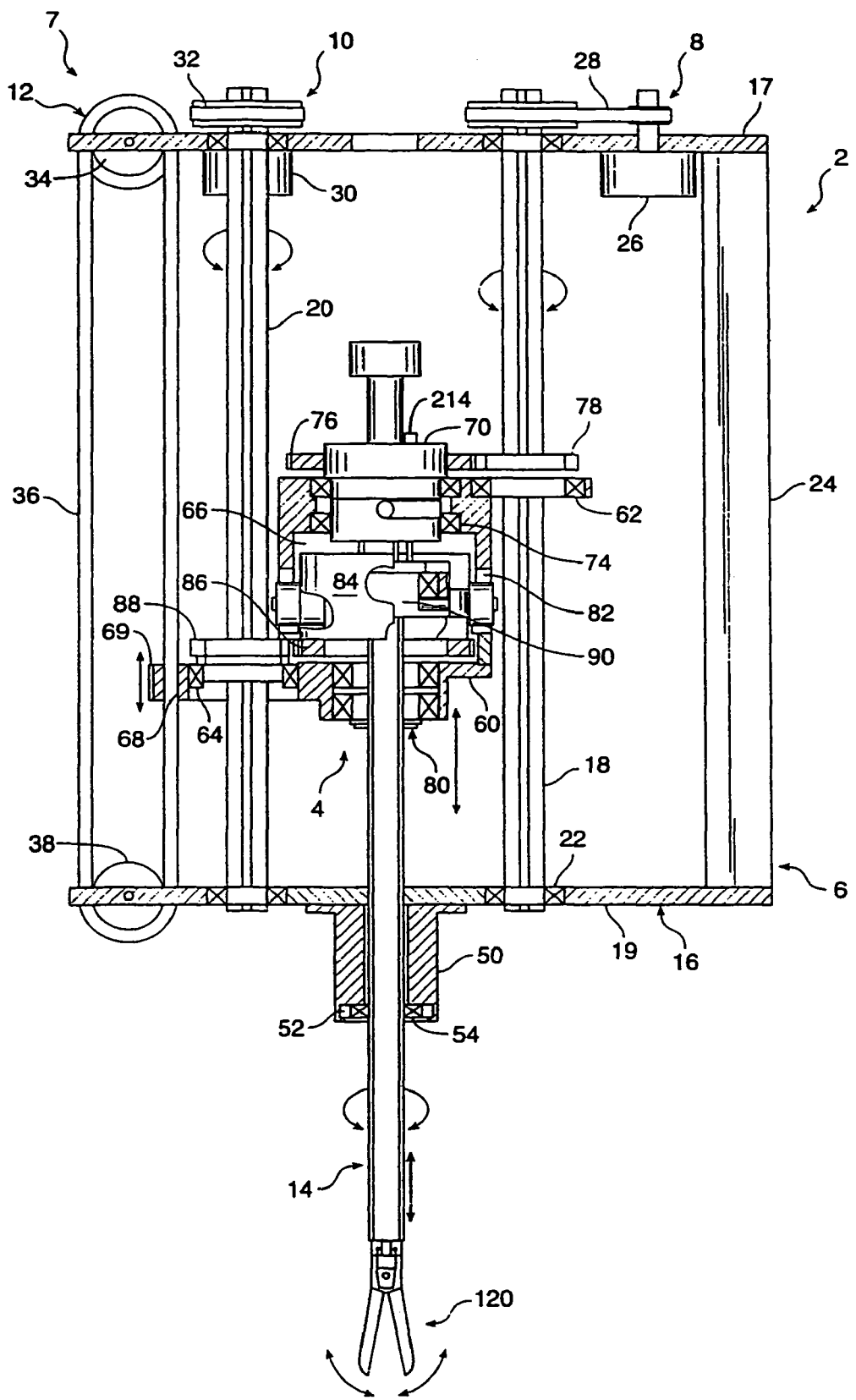
FIG. 1 is a partial sectional elevational view of a robotic endoscopic surgical instrument mounted to a manipulator assembly according to the present invention.

Referring to the drawings in detail, wherein like numerals indicate like elements, a manipulator assembly 2 is illustrated according to the principles of the invention. Manipulator assembly 2 generally includes an instrument holder 4 removably mounted to a base 6 and a drive assembly 7 for manipulating a surgical instrument 14 releasably coupled to instrument holder 4.

Referring to FIG. 1, base 6 comprises a frame 16 having proximal and distal elongate support members 17, 19 and first and second ball-spline shafts 18, 20 rotatably coupled to support members 17, 19 via bearings 22. Frame 16 further includes a support bracket 24 for attaching manipulator assembly 2 to a remote center positioner 300, as discussed in more detail below (see FIG. 9). Drive assembly 7 comprises first, second and third drives 8, 10, 12, which are mounted to frame 16 and configured to provide three degrees of freedom to surgical instrument 14. In the preferred embodiment, first drive 8 rotates instrument 14 around its own axis, second drive 10 actuates an end effector 120 on the distal end of instrument 14 and third drive 12 axially displaces instrument 14 with respect to frame 16. Of course, it will be readily recognized by those skilled in the art that other configurations are possible. For example, assembly 2 may include additional drives for providing additional degrees of freedom to surgical instrument 14, such as rotation and flexion of an instrument wrist.

First drive 8 comprises a rotation drive motor 26 fixed to frame 16 and coupled to first shaft 18 by a drive belt 28 for rotating first shaft 18 with respect to frame 16. Second drive 10 comprises a gripper drive motor 30 fixed to frame 16, and coupled to second shaft 20 by a drive belt 32 for rotating second shaft 20 with respect to frame 16. Third drive 12 comprises a vertical drive motor 34 coupled to instrument holder 4 via a drive belt 36 and two pulleys 38 for axially displacing instrument holder 4 with respect to frame 16. Drive motors 26, 30, 34 are preferably coupled to a controller mechanism via servo-control electronics (not shown) to form a telerobotic system for operating surgical instrument 14 by remote control. The drive motors follow the motions of a surgeon's hands as he/she manipulates input control devices at a location that may be remote from the patient. A suitable telerobotic system for controlling the drive motors is described in commonly assigned co-pending application Ser. No. 08/623,932 filed Jan. 21, 1992 TELEOPERATOR SYSTEM AND METHOD WITH TELEPRESENCE, which is incorporated herein by reference.

The above described telerobotic servo system preferably has a servo bandwidth with a 3 dB cut off frequency of at least 10 hz so that the system can quickly and accurately respond to the rapid hand motions used by the surgeon. To operate effectively with this system, instrument holder 4 has a relatively low inertia and drive motors 26, 30, 34 have relatively low ratio gear or pulley couplings.

In a specific embodiment, surgical instrument 14 is an endoscopic instrument configured for introduction through a percutaneous penetration into a body cavity, such as the abdominal or thoracic cavity. In this embodiment, manipulator assembly 2 supports a cannula 50 on distal support member 19 of frame 16 for placement in the entry incision during an endoscopic surgical procedure (note that cannula 50 is illustrated schematically in FIG. 1 and will typically be much longer). Cannula 50 is preferably a conventional gas sealing trocar sleeve adapted for laparoscopic surgery, such as colon resection and Nissen fundoplication.

As shown in FIG. 1, cannula 50 preferably includes a force sensing element 52, such as a strain gauge or force-sensing resistor, mounted to an annular bearing 54 within cannula 50. Bearing 54 supports instrument 14 during surgery, allowing the instrument to rotate and move axially through the central bore of bearing 54. Bearing 54 transmits lateral forces exerted by the instrument 14 to force sensing element 52, which is operably connected to the controller mechanism for transmitting these forces to the input control devices (not shown) held by the surgeon in the telerobotic system. In this manner, forces acting on instrument 14 can be detected without disturbances from forces acting on cannula 50, such as the tissue surrounding the surgical incision, or by gravity and inertial forces acting on manipulator assembly 2. This facilitates the use of manipulator assembly in a robotic system because the surgeon will directly sense the forces acting against the end of instrument 14. Of course, the gravitational forces acting on the distal end of instrument 14 will also be detected by force sensing element 52. However, these forces would also be sensed by the surgeon during direct manipulation of the instrument.

As shown in FIG. 1, instrument holder 4 comprises a chassis 60 mounted on shafts 18, 20 via ball-spline bearings 62, 64 so that chassis 60 may move axially with respect to shafts 18, 20, but is prevented from rotating with shafts 18, 20. Chassis 60 is preferably constructed of a material that will withstand exposure to high temperature sterilization processes, such as stainless steel, so that chassis 60 can be sterilized after a surgical procedure. Chassis 60 includes a central cavity 66 for receiving surgical instrument 14 and an arm 68 laterally extending from chassis 60. Arm 68 is fixed to drive belt 36 so that rotation of drive belt 36 moves instrument holder 4 in the axial direction along shafts 18; 20.

Figure 1A:
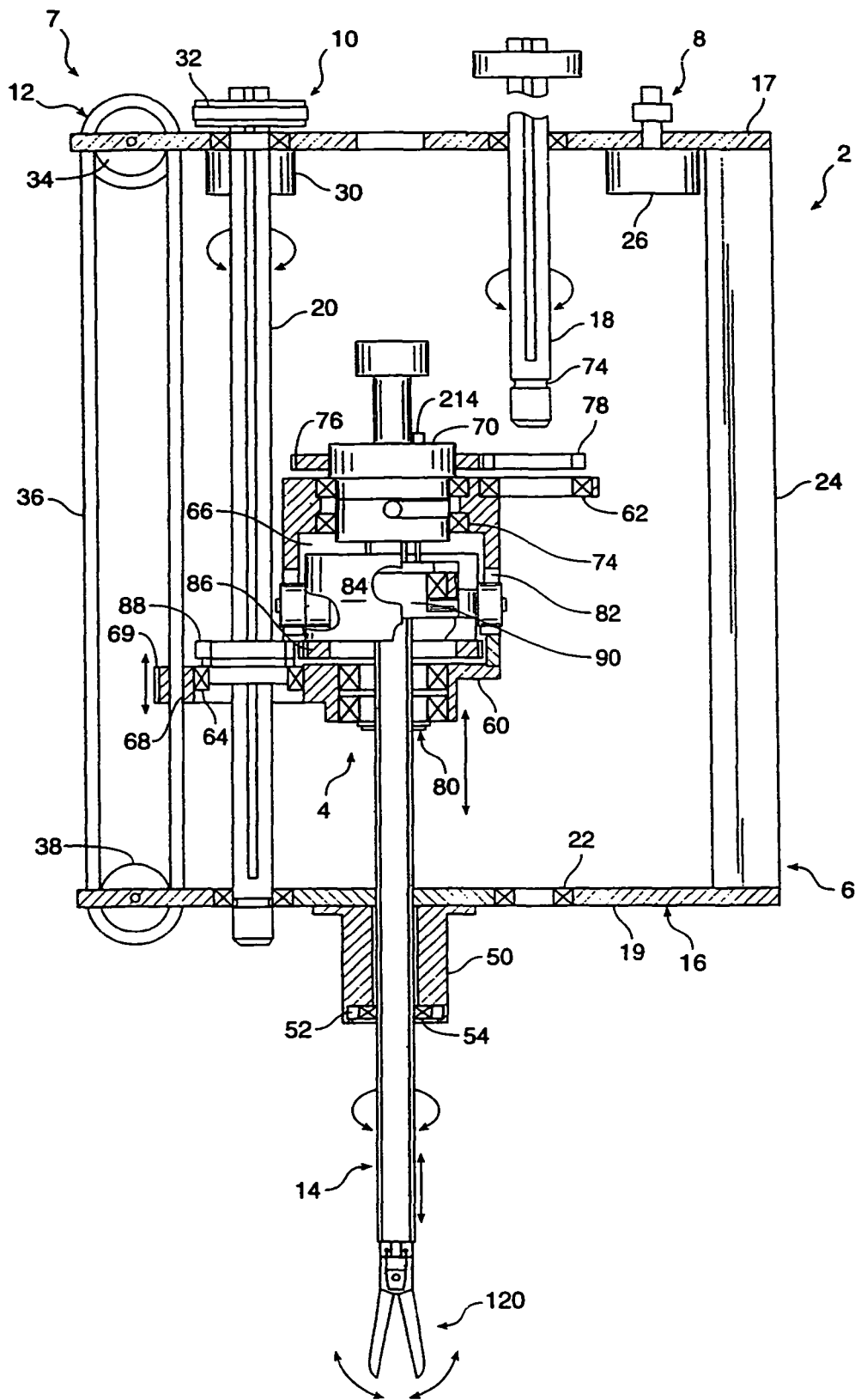
FIG. 1A is a partial sectional elevational view of the manipulator assembly of FIG. 1 illustrating the removal of an instrument holder from the rest of the assembly.
Figure 7:
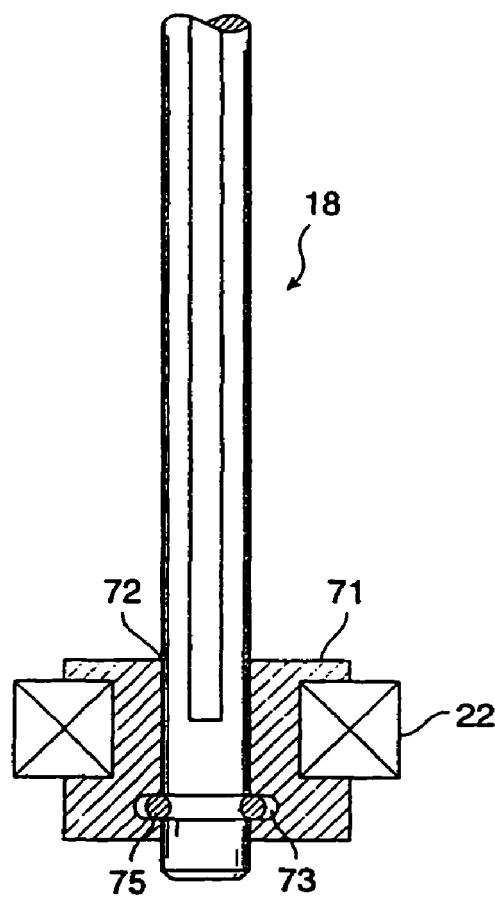
FIG. 7 is an enlarged detail of a portion of the frame of the manipulator assembly of FIG. 1 illustrating a coupling mechanism for removing the shafts from the frame.

Instrument holder 4 is removably coupled to base 6 and the drive motors so that the entire holder 4 can be removed and sterilized by conventional methods, such as steam, heat and pressure, chemicals, etc. In the preferred configuration, arm 68 includes a toggle switch 69 that can be rotated to release arm 68 from drive belt 36 (FIG. 1). In addition, shafts 18, 20 are removably coupled to bearings 22 so that the shafts can be axially withdrawn from support members 17, 19 of frame 16, as shown in FIG. 1A. To this end, the distal bearings 22 preferably include a coupling mechanism for allowing the removal of shafts 18, 20. As shown in FIG. 7, distal support member 19 includes a support collar 71 within each distal bearing 22 having an inner bore 72 for passage of one of the shafts 18, 20. Each support collar 71 has an internal groove 73 and shafts 18, 20 each have an annular groove 74 (see FIG. 1A) near their lower ends that is aligned with internal grooves 73 when the shafts are suitably mounted within frame 16 (FIG. 1). A spring clip 75 is positioned within each internal groove 73 to hold each shaft 18, 20 within the respective support collar 71. Spring clip 74 has a discontinuity (not shown) to allow removal of shafts 18, 20 upon the application of a threshold axial force on the shafts.

To remove instrument holder 4 from base 6, the operator rotates toggle switch 69 to release arm 68 from drive belt 36 and removes drive belts 28, 32 from drives 8, 10. As shown in FIG. 1A, the operator holds instrument holder 4 and pulls shafts 18, 20 upwards, providing enough force to release spring clips 75. Shafts 18, 20 will disengage from distal bearings 22 and slide through ball-spline bearings 62, 64 so that instrument holder 4 is disconnected from base 6. It should be understood that the invention is not limited to the above described means for removably coupling instrument holder 4 to base 6 and drive assembly 7. For example, distal support member 19 may be removably coupled to the rest of frame 16 so that the surgeon simply removes member 19 and slides holder down and off shafts 18, 20. Proximal support member 17 may be removably coupled to frame 16 in a similar manner. Alternatively, the drive motors may be housed in a separate servo-box (not shown) that is removably attached to base 6. In this configuration, the servo-box would be removed from base 6 so that the entire base 6, together with holder 4, can be sterilized.

The lower portion of base 6 (including distal support member 19) may also be sterilized to decontaminate those parts that come into contact with holder 4 or instrument 14 (e.g., by dipping the lower portion of base 6 into a sterilizing bath). To facilitate this type of sterilization, shafts 18, 20 will preferably be somewhat longer than shown in FIG. 1 so that the upper portion of base 6, including drive assembly 7, is disposed sufficiently away from holder 4 and instrument 14. In this manner, the surgical manipulator can be easily sterilized after a surgical procedure without damaging the drive motors or the electrical connections required for the telerobotic system.

Instrument holder 4 further includes an instrument support 70 (see detail in FIG. 3A), for releasably coupling surgical instrument 14 to the manipulator assembly. Instrument support 70 is rotatably mounted within chassis 60 via mounting bearings 74 so that support 70 and the instrument can be rotated therein. As shown in FIG. 1, support 70 is circumscribed by an annular ring gear 76 having teeth that mesh with the teeth of a drive gear 78 mounted to first shaft 18. Drive gear 78 is configured around first shaft 18 such that it will rotate with first shaft 18, thereby rotating instrument support 70 and the surgical instrument therewith. Drive gear 78 is also configured to move axially with respect to first shaft 18 to allow axial movement of instrument holder 4 with respect to frame 16.

Instrument holder 4 further includes an actuator driver 80 (see detail in FIG. 5) movably mounted within axial guide slots 82 on either side of chassis 60. Actuator driver 80 comprises a helical actuator 84 (see detail in FIG. 6B) having a ring gear 86 that meshes with a gripper drive gear 88 mounted to second shaft 20. Rotation of second shaft 20 causes rotation of gripper drive gear 88, thereby rotating ring gear 86 and helical actuator 84 within chassis 60. Actuator driver 80 further includes an actuator carriage assembly 90 (see detail in FIG. 6A) for releasably coupling an end effector actuator of surgical instrument 14 to instrument holder 4 (see FIG. 2). Carriage assembly 90 is mounted within helical actuator 84 and chassis 60 such that rotation of helical actuator 84 causes a corresponding axial movement of carriage assembly 90 with respect to chassis 60, as discussed in greater detail below.

Figure 2A:
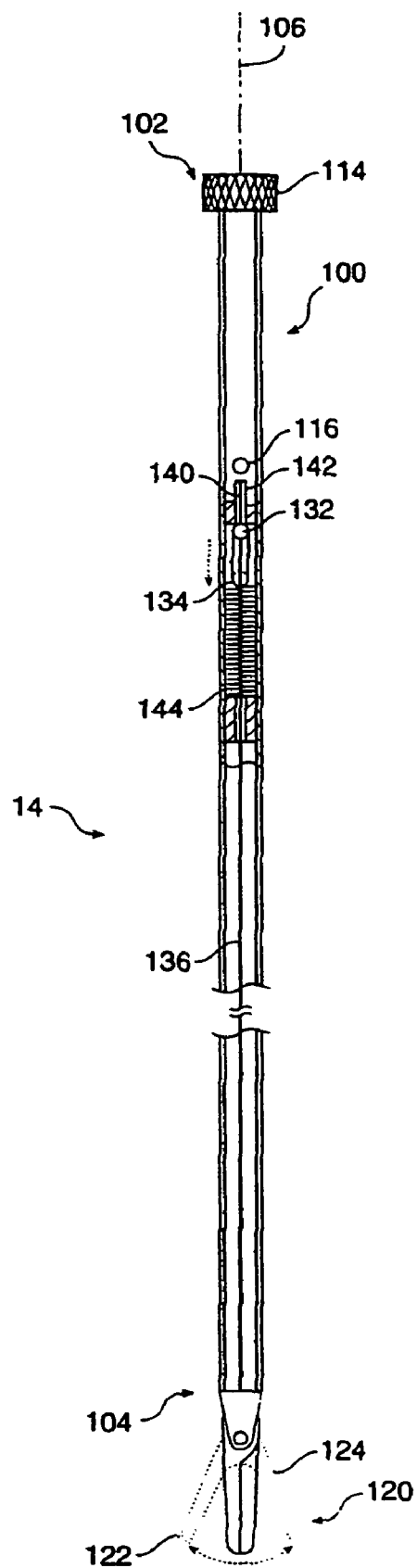
FIGS. 2A and 2B are enlarged side and front cross-sectional views, respectively, of the surgical instrument of FIG. 1.
Figure 2B:
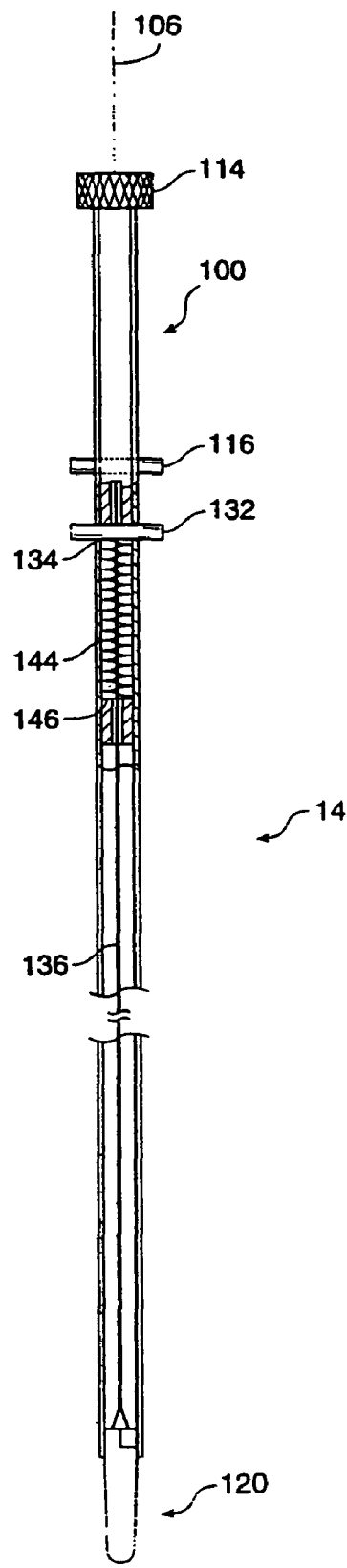

FIGS. 2A and 2B illustrate a specific embodiment of an endoscopic surgical instrument 14 capable of being operated by a motorized manipulator, such as manipulator assembly 2, for telerobotic surgery. Surgical instrument 14 can be a variety of conventional endoscopic instruments adapted for delivery through a percutaneous penetration into a body cavity, such as tissue graspers, needle drivers, microscissors, electrocautery dissectors, etc. In the preferred embodiment, instrument 14 is a tissue grasper comprising a shaft 100 having a proximal end 102, a distal end 104 and a longitudinal axis 106 therebetween. A knurled handle 114 is attached to proximal end 102 of shaft 100 to facilitate manipulation of instrument 14.

Shaft 100 is preferably a stainless steel tube having an outer diameter in the range of 2-10 mm, usually 4-8 mm, so as to fit within a cannula having an internal diameter in the range of 2-15 mm. Shaft 100 can also be introduced directly through a percutaneous incision in the patient. Shaft 100 has a length selected to reach a target site in a body cavity, such as the abdomen, and to extend sufficiently out of the body cavity to facilitate easy manipulation of surgical instrument 14. Thus, shaft 100 should be at least between 10 cm and 40 cm and is preferably between 17 cm and 30 cm. It should be noted that although shaft 100 is shown as having a circular cross-sectional shape in the drawings, shaft 100 could alternatively have a rectangular, triangular, oval or channel cross-sectional shape.

In a specific configuration, shaft 100 includes a mounting means for releasably coupling surgical instrument 14 to instrument support 70 and first drive 8 of manipulator assembly 2. In the preferred embodiment, mounting means comprises a pair of opposed mounting pins 116 extending laterally outward from shaft 100. Mounting pins 116 are rigidly connected to shaft 100 and are adapted for engaging a twist-lock interface on instrument support 70, as discussed in detail below. It should be understood that the invention is not limited to a pair of opposing pins and mounting means can include a single mounting pin or a plurality of pins extending circumferentially around shaft. Alternatively, pins 116 may have a variety of other shapes, such as spherical or annular, if desired.

Instrument 14 includes an end effector 120 extending from distal end 104 for engaging a tissue structure on the patient, such as the abdomen during laparoscopic surgery. In the preferred embodiment, end effector 120 comprises a pair of jaws 122, 124 that are movable between open and closed positions for grasping a blood vessel, holding a suture, etc. Jaws 122, 124 preferably have transverse grooves or other textural features (not shown) on opposing surfaces to facilitate gripping of the tissue structure. To avoid the possibility of damaging the tissue to which jaws 122, 124 are applied, the jaws may also include atraumatic means (not shown), such as elastomeric sleeves made of rubber, foam or surgical gauze wrapped around jaws 122, 124.

Figure 4:
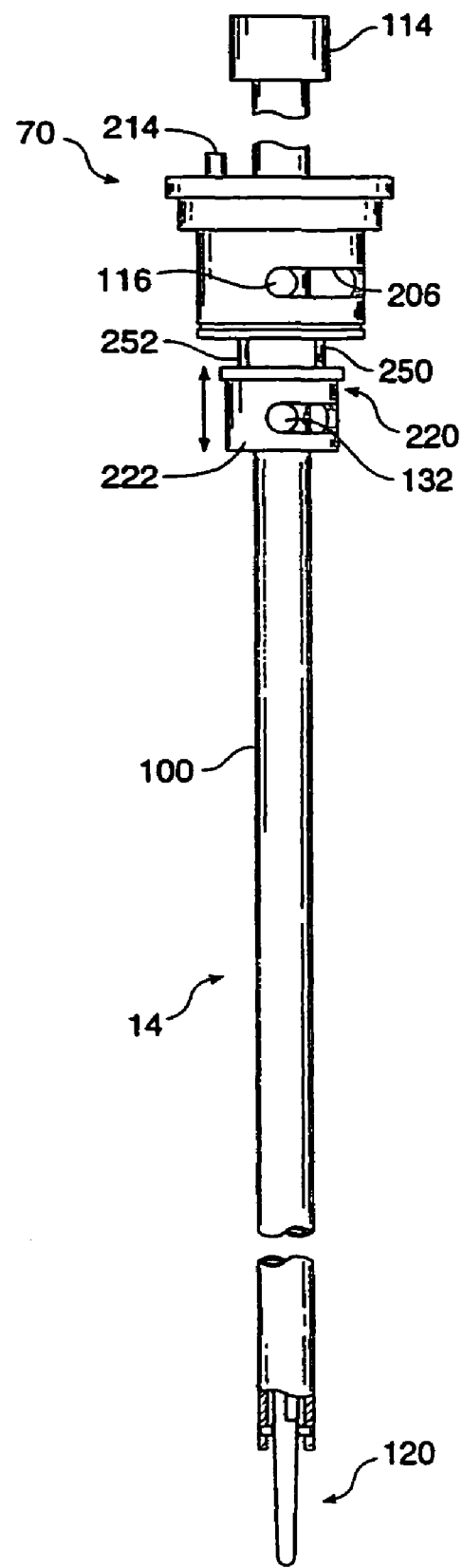
FIG. 4 is a front elevational view of the surgical instrument mounted within the instrument support and actuator pin catch of FIGS. 3A and 3B.

To move jaws 122, 124 between the open and closed positions, instrument 14 includes an end effector actuator releasably coupled to actuator driver 80 and second drive 10 of manipulation assembly 2 (see FIG. 4). In the preferred embodiment, end effector actuator comprises a pair of opposed actuator pins 132 laterally protruding from axially extending slots 134 in shaft 100. Actuator pins 132 are coupled to an elongate rod 136 slidably disposed within an inner lumen 138 of shaft 100. Actuator pins 132 are slidable within slots 134 so that rod 136 is axially movable with respect to shaft 100 and mounting pins 116 to open and close jaws 122, 124, as is conventional in the art. Elongate rod 136 has a proximal portion 140 that is disposed within an inner lumen 142 within shaft 100 to prevent actuator pins 132 from moving in the laterally direction and to ensure that rod 136 remains generally centered within shaft 100 during a surgical procedure.

Jaws 122, 124 are preferably biased into the closed positioned by an annular compression spring 144 positioned within shaft 100 between actuator pins 132 and an annular disc 146 fixed to the inside surface of shaft 100. During endoscopic procedures, this allows the surgical team to introduce jaws 122, 124 through cannula 50 (or any other type of percutaneous penetration) and into the body cavity without getting stuck within cannula 50 or damaging surrounding tissue.

Figure 3A:
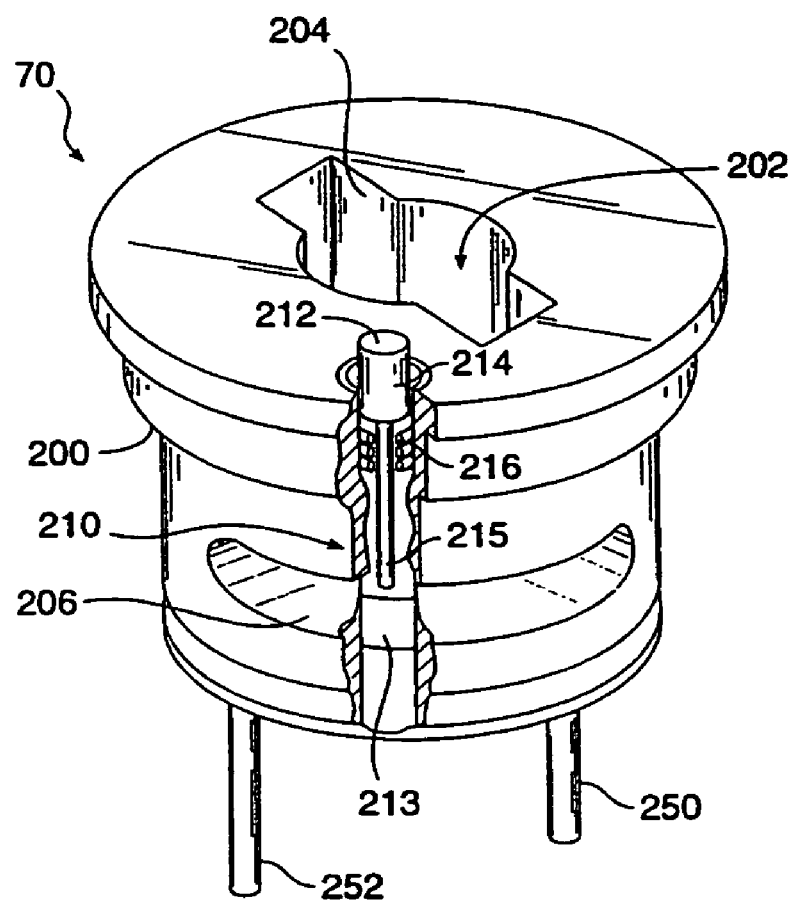
FIGS. 3A and 3B are perspective views of an instrument support and an actuator pin catch, respectively, for releasably mounting the surgical instrument to the manipulator assembly.
Figure 3B:
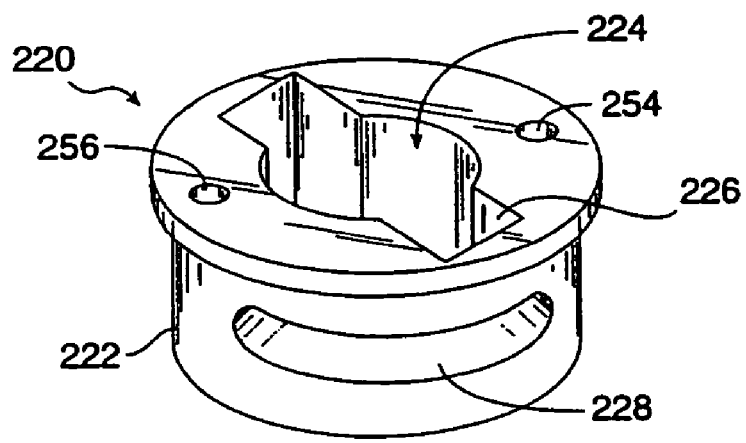

FIGS. 3A, 3B and 4 illustrate a twist lock mechanism for releasably connecting surgical instrument 14 to manipulator assembly 2 so that different instruments may be rapidly changed during an endoscopic surgical procedure. As shown in FIG. 3A, instrument support 70 comprises an annular collar 200 defining a central bore 202 for receiving shaft 100 of surgical instrument 14. Collar 200 further defines an axially extending slot 204 in communication with bore 202 and sized to allow mounting and actuator pins 116, 132 of instrument 14 to slide therethrough (see FIG. 4). Two locking slots 20'6 are cut into annular collar 200 at a transverse angle, preferably about 900, to axially extending slot 204 (note that only one of the locking slots are shown in FIG. 3A). Locking slots 206 intersect slot 204 near the center of annular collar 200 and extend circumferentially around bore 202, preferably about 90.degree., to allow rotation of both mounting pins 116 therethrough, as discussed below.

Figure 8:
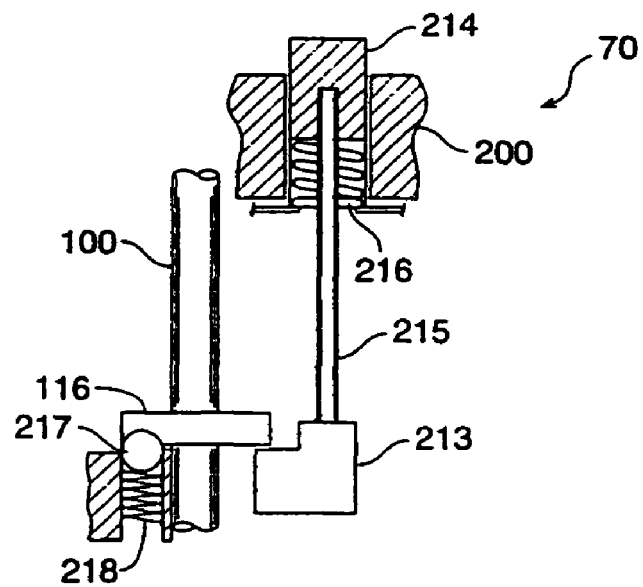
FIG. 8 is a partial cross-sectional view of the instrument support of FIG. 3A illustrating a locking mechanism for a twist lock interface according to the present invention.

As shown in FIGS. 3A and 8, instrument support 70 further comprises means for locking mounting pins 116 into locking slots 206 so that the instrument cannot be accidently twisted and thereby disengaged from instrument support 70 during surgery. Preferably, the locking means comprises a latch assembly having a plunger 210 slidably disposed within a hole 212 in collar 200, as shown in FIG. 3A. Plunger 210 comprises an L-shaped latch 213 coupled to a release button 214 by a rod 215 extending through hole 212. Plunger 210 is movable between a first position, where latch 213 is not disposed within locking slots 206 so that mounting pins 116 are free to rotate therethrough, and a second position, where latch 213 is at least partially disposed within one of the locking slots 206 so as to prevent rotation of mounting pins 116: Latch 213 is preferably biased into the second or locked position by a compression spring 216.

Button 214 is disposed on the upper surface of support 70 for manual actuation by the surgeon or automatic actuation by base 6. Preferably, when instrument holder 4 is moved to its most proximal position (see FIG. 1), proximal support member 17 of frame 16 depresses release switch 214 to move latch 213 into the first or open position. With this configuration, instruments can be exchanged only when the instrument holder 4 is in the most proximal position, where shaft 100 of instrument 14 is easily accessible. In addition, this prevents the accidental release of the instrument when its distal end has penetrated cannula 50 and is disposed within the body cavity.

The intersecting axial and locking slots 204, 206 form an interface for releasably coupling mounting pins 116 of surgical instrument 14 to instrument holder 4. To insert instrument 14, the surgeon aligns mounting pins 116 with axial slot 204 and slides the instrument through bore 202 of annular collar 200 until mounting pins 116 are aligned with locking slots 206, as shown in FIG. 4. The instrument is then rotated a sufficient distance, preferably about a ¼ turn, through locking slots 206 so that the pins are no longer aligned with axial slot 204. When instrument 14 is moved distally, switch 214 is released (FIG. 1) and latch 213 moves into locking slots 206 to prevent mounting pins 116 from rotating back into alignment with axial slot 204 so that instrument 14 is secured to instrument support 70. It should be noted that a single mounting pin may be utilized with the above described configuration to lock the surgical instrument to the support. However, two opposing pins are preferred because this configuration reduces torsional forces on the inner surface of locking slots 206.

As shown in FIG. 8, the locking means preferably includes a ball detent 217 disposed within collar 200. Ball detent 217 is biased upward into one of the locking slots 206 by a spring 218. Ball detent 217 serves to temporarily capture mounting pins 116 in a position rotated about 90.degree. from alignment with axial slot 204. This ensures that the mounting pins will be completely rotated into the proper position (i.e., out of the way of latch 213) when instrument 14 is twisted into instrument holder. Otherwise, when switch 214 is released, latch 213 could become engaged with mounting pins 216 so that the latch is unable to move completely into the locked position, thereby potentially causing the accidental release of instrument 14 during surgery.

Figure 5:
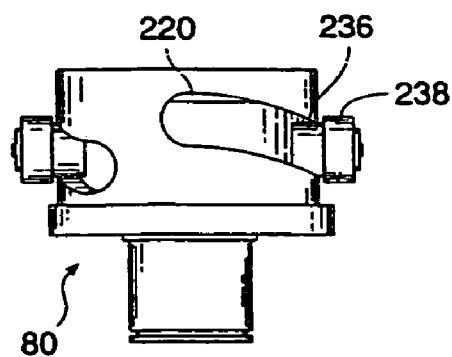
FIG. 5 is a front elevational view of an actuator driver for providing axial movement of the actuator pin catch of FIG. 3B.

As shown in FIGS. 3B, 4 and 5, actuator driver 80 of instrument holder 4 further comprises an actuator pin catch 220 for releasably holding and moving actuator pins 132 of instrument 14. Actuator pin catch 220 is constructed similarly to instrument support 70 (FIG. 3A), comprising an annular collar 222 that defines a bore 224 for receiving shaft 100 and an axially extending slot 226 for receiving actuator pins 132. A locking slot 228 is cut into actuator pin catch 220 at a 90.degree. angle so that actuator pins can be rotated into the lock slot to couple actuator pins 132 to actuator driver 66, as discussed above in reference to the mounting pins. It should be noted that slot 226 need not extend completely through collar 222 since actuator pins 132 are located distally of mounting pins 116 (the instrument is preferably inserted jaws first). Of course, actuator and mounting pins 132, 116 may be reversed so that the mounting pins are distal to the actuator pins, if desired.

Figure 6A:
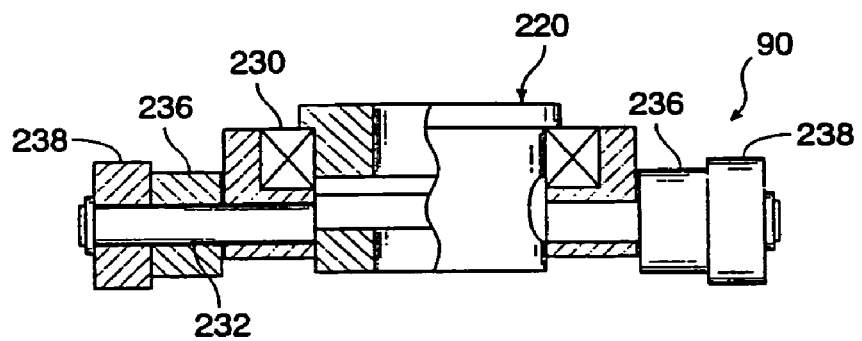
FIGS. 6A and 6B are enlarged cross-sectional views of an actuator carriage assembly and a helical actuator of the actuator driver of FIG. 5.

Referring to FIG. 6A, actuator pin catch 220 is rotatably mounted on a ball bearing 230 in actuator carriage assembly 90. Bearing 230 allows the pin catch 220 to rotate freely in carriage assembly 90 while preventing relative axial motion. Therefore, when instrument 14 is rotated by first drive 8, actuator pins 132 will rotate within carriage assembly 90. Carriage assembly 90 further comprises two sets of axles 232 for rotatably supporting a pair of inner rollers 236 and a pair of outer rollers 238. As shown in FIG. 1, outer rollers 238 are slidably disposed within axial guide slots 82 of chassis 60 to prevent rotation of carriage assembly 90 with respect to chassis 60. Inner and outer rollers 236, 238 cooperate with helical actuator 84 and chassis 60 of instrument holder 4 to move axially with respect to the holder, thereby axially moving pin catch 220 and actuator pins 132 therewith relative to shaft 100 of instrument 14 (which actuates jaws 122, 124, as discussed above).

Figure 6B:
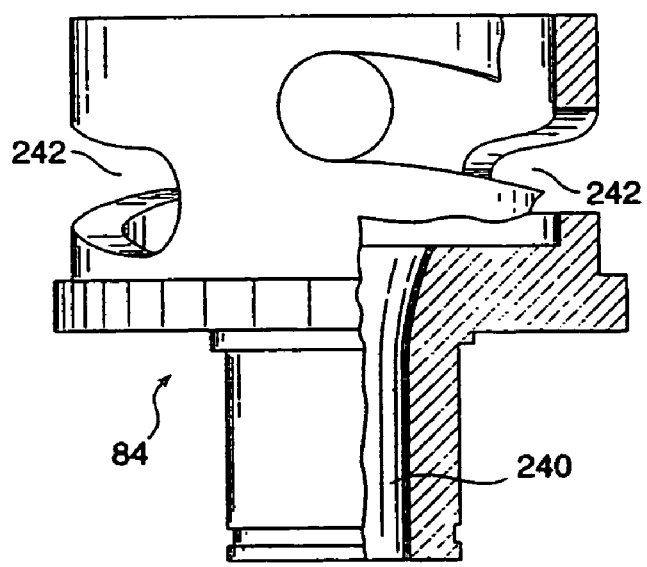

As shown in FIG. 6B, helical actuator 84 includes a central bore 240 for receiving carriage assembly 90 and surgical instrument 14 and two opposing helical tracks 242, 244 each extending circumferentially around helical actuator 84 (preferably slightly less than 180.degree.) for receiving inner rollers 236 of carriage assembly 90, as shown in FIG. 5. With outer rollers 238 constrained in axial guide slots 82 of chassis 60, rotation of helical actuator 84 causes carriage assembly 90 (and actuator pin catch 220) to move up or down, depending on the sense of the rotation. Because of the symmetrical design of helical actuator 84, the actuation force applied by second driver 10 will not generate any effective side loads on instrument 14, which avoids frictional coupling with other degrees of freedom such as axial (third driver 12) and rotation (first driver 8). In the preferred embodiment; helical tracks 242, 244 have a pitch selected such that the mechanism can be easily back-driven, allowing grip forces to be sensed in a position-served teleoperation system.

As shown in FIGS. 3A and 3B, instrument holder 4 further includes a pair of axial guide pins 250, 252 fixed to instrument support 70. Actuator pin catch 220 has a pair of openings 254, 256 for receiving guide pins 250, 252. Guide pins 250, 252 prevent relative rotation between pin catch 220 and support 70 (so that actuator and mounting pins 116, 132 can both rotate with the instrument) and allow axial movement relative to each other (so that end effector 120 can be actuated by axial movement of actuator pins 132).

Figure 9:
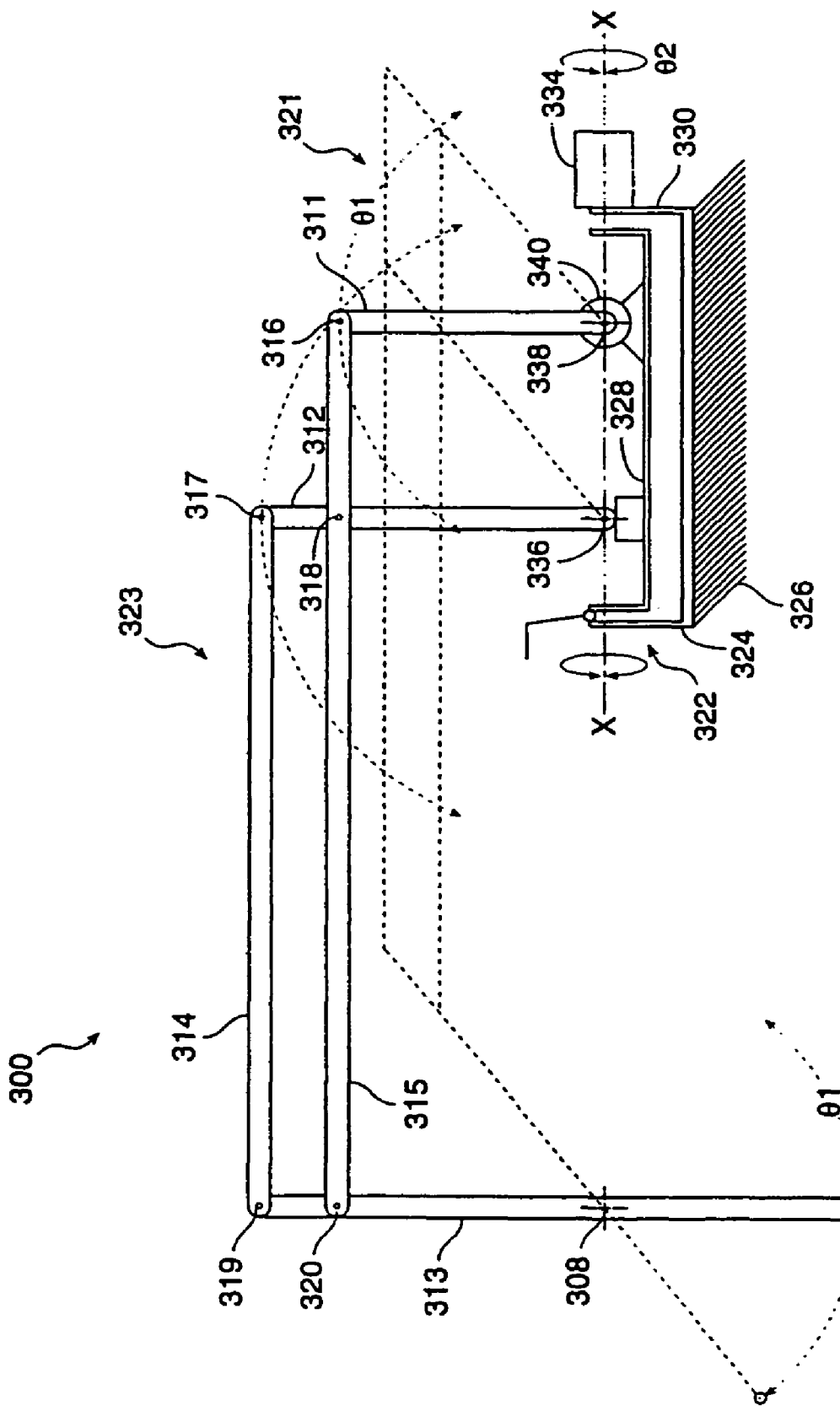
FIG. 9 is an elevational view of a remote center positioner for holding the manipulator assembly of FIG. 1.

FIG. 9 is an elevational view of a remote center positioner 300 which can be used to support manipulator assembly 2 above the patient (note that support manipulator 2 is not shown in FIG. 8). Remote center positioner 300 provides two degrees of freedom for positioning manipulator assembly 2, constraining it to rotate about a point 308 coincident with the entry incision. Preferably, point 308 will be approximately the center of bearing 54 in cannula 50 (FIG. 1). A more complete description of remote center positioner 300 is described in commonly assigned co-pending application Ser. No. 08/062,404 filed May 14, 1993 REMOTE CENTER POSITIONER, which is incorporated herein by reference.

A first linkage means is indicated generally by the numeral 321 and a second linkage in the form of a parallelogram is indicated by the numeral 323. The first linkage means is pivotally mounted on a base plate for rotation about an x-x axis. The second linkage means is pivotally connected to the first linkage means and is adapted to move in a plane parallel to the first linkage. Five link members (including extensions thereof), 311, 312, 313, 314, and 315 are connected together with pivot joints 316-320. A portion of element 313 extends beyond pivot 320 of the parallelogram linkage. The parallelogram linkage has an operating end at link member 313 and a driving end at link member 312. The elongated element 313 may, as desired later, carry a surgical instrument or other device, such as support bracket 24 of manipulator assembly 2. The pivot joints allow relative motion of the link members only in the plane containing them.

A parallelogram linkage is formed by corresponding link members 314, 315 and link members 312 and 313. The portions of link members 314 and 315 of the parallelogram are of equal length as are the portions of members 312 and 313 of the parallelogram. These members are connected together in a parallelogram for relative movement only in the plane formed by the members. A rotatable joint generally indicated by the numeral 322 is connected to a suitable base 324. The rotatable joint 322 is mounted on a base plate 326 adapted to be fixedly mounted to the base support means 324. A pivot plate 328 is pivotally mounted to base plate 326 by suitable means at, such as, pivots 330, 332. Thus pivot plate 328 may be rotated about axis x-x through a desired angle 62. This may be accomplished manually or by a suitable pivot drive motor 334.

A first linkage is pivotally mounted on the pivot plate 328 of the rotatable joint 322. The linkage elements 311, 312 and the link members are relatively stiff or inflexible so that they may adequately support an instrument used in surgical operations. Rods made of aluminum or other metal are useful as such links. The linkage elements 311 and 312 are pivotally mounted on base plate 328 for rotation with respect to the rotatable joint by pivots 336 and 338. At least one of the pivots 336, 338 is positioned so that its axis of rotation is normal to and intersects the x-x axis. Movement may occur manually or may occur using a linkage drive motor 340. The first linkage is also shaped in the form of a parallelogram formed by linkage elements 311, and 312; the portion of link member 315 connected thereto by pivots 316, 318; and base plate 328. One of the link members 315 is thus utilized in both the first 321 and second 323 linkage means. Linkage element 312 also forms a common link of both the first linkage means 321 and the second linkage means 323. In accordance with the invention, a remote center of spherical rotation 308 is provided by the above described embodiment of apparatus when the linkage element 311 is rotated and/or when pivot plate 328 is rotated about axis x-x. Thus, the end of element 313 can be moved through desired angles 81 and 92 or rotated about its own axis, while the remote center of rotation remains at the same location.

FIG. 9 also shows an inclinometer 350 attached to the base of remote center positioner 300. The remote center positioner may be mounted at an arbitrary orientation with respect to vertical depending on the particular surgery to be performed, and inclinometer 350 can be used to measure this orientation. The measured orientation can be used to calculate and implement servo control signals necessary to control the telerobotic system so as to prevent gravitational forces acting on the system mechanisms from being felt by the surgeon.

Figure 10:
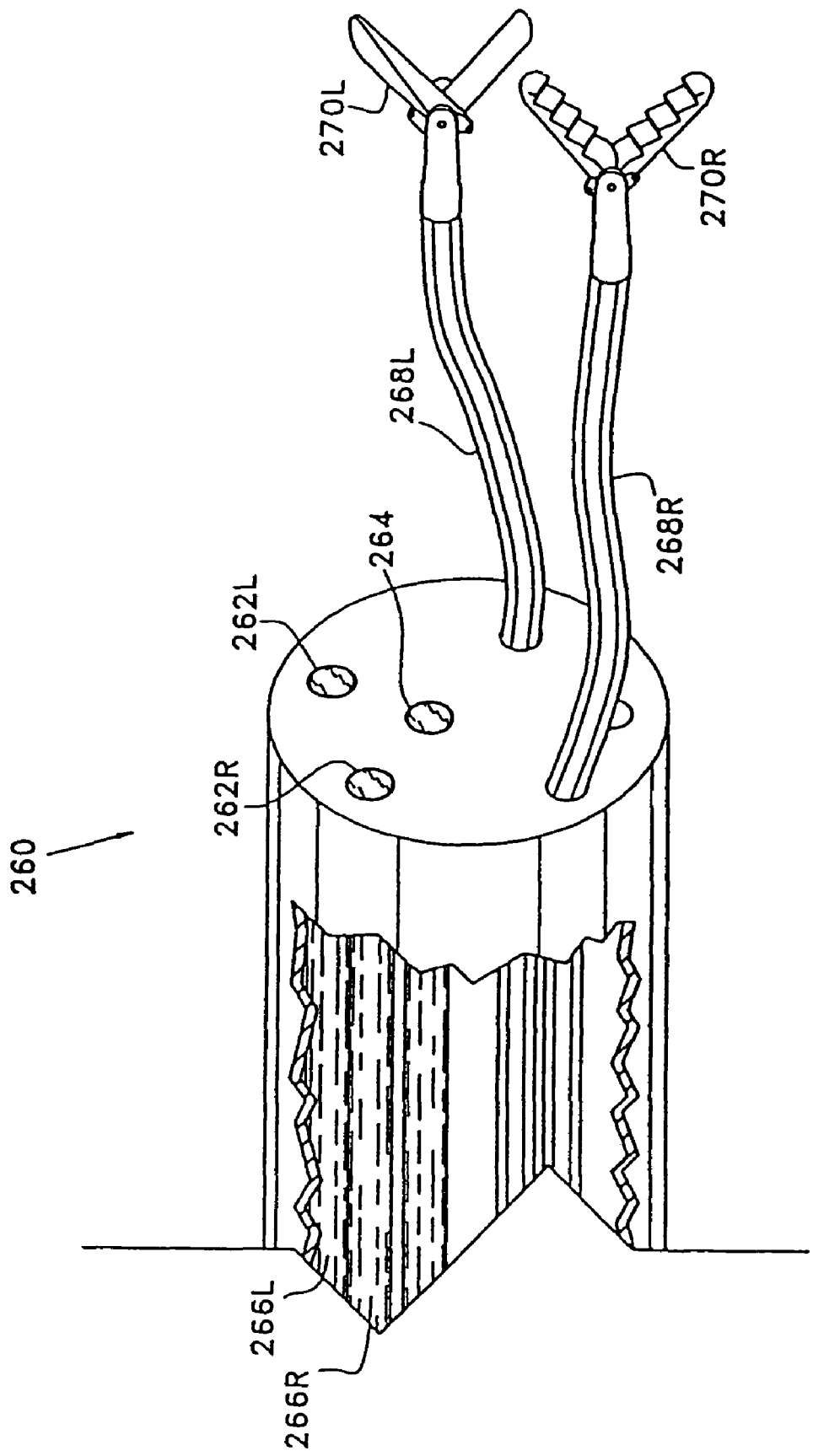
FIG. 10 shows a fragmentary portion of the insertion portion of an endoscope for use with the present invention.

Reference now is made to FIG. 10 wherein the distal end portion or tip, 260 of the insertion section of an endoscope is shown which is a substantially the same type as shown in the above-mentioned publication entitled "Introduction to a New Project for National Research and Development Program (Large-Scale Project) in FY 1991" which endoscope may be used in the practice of the present invention. The insertion end of the endoscope includes a pair of spaced viewing windows 262R and 262L and an illumination source 264 for viewing and illuminating a workspace to be observed. Light received at the windows is focused by objective lens means, not shown, and transmitted through fiber-optic bundles to a pair of cameras at the operating end of the endoscope, now shown. The camera outputs are converted to a three-dimensional image of the workspace which image is located adjacent hand-operated means at the operator's station, now shown. Right and left steerable catheters 268R and 268L pass through accessory channels in the endoscope body, which catheters are adapted for extension form the distal end portion, as illustrated. End effectors 270R and 270L are provided at the ends of the catheters which may comprise conventional endoscopic instruments. Force sensors, not shown, also are inserted through the endoscope channels. Steerible catheters which include control wires for controlling bending of the catheters and operation of an end effector suitable for use with this invention are well known. Control motors for operation of the control wires are provided at the operating end of the endoscope, which motors are included in a servomechanism of a type described in U.S. patent application Ser. No. 07/823, 932 for operation of the steerable catheters and associated end effectors from a remote operator's station. As with the other embodiments described in U.S. patent application Ser. No. 07/823,932, the interfacing computer in the servomechanism system remaps the operator's hand motion into the coordinate system of the end effectors, and images of the end effectors are viewable adjacent the hand-operated controllers. With this embodiment, the operator has the sensation of reaching through the endoscope to put his hands directly on the end effectors for control thereof. Endoscopes of different types may be employed in this embodiment of the invention so long as they include one or more accessory channels for use in control of end effectors means, and suitable viewing means for use in providing a visual display of the workspace. For example, gastric, colonscopic, and like type, endoscopes may be employed.

Variations and changes may be made by others without departing from the spirit of the present invention. For example, it should be understood that the present invention is not limited to endoscopic surgery. In fact, instrument holder 4, along with a telerobotic control mechanism, would be particularly useful during open surgical procedures, allowing a surgeon to perform an operation from a remote location, such as a different room or a completely different hospital.

What is claimed is:

1. A surgical instrument comprising:
   a shaft having a distal end and a proximal end;
   a formation at the distal end of said shaft, said formation movable relative to said shaft in a first degree of freedom;
   at least one elongate element connected to the formation to cause movement in said first degree of freedom in response to movement of said at least one elongate element;
   at least one actuated body disposed at the proximal end of said shaft, said at least one actuated body coupled to said at least one elongate element such that driving said at least one actuated body causes movement of said at least one elongate element;
   said shaft detachably coupleable to an actuating mechanism for selectively driving said at least one actuated body; said shaft further detachably coupleable to a robotic manipulator arm for moving said shaft in at least one degree of freedom, said manipulator arm supporting said actuating mechanism;
   wherein said robotic manipulator arm is tart of a remote centering mechanism operable to pivot said shaft about a fixed insertion point.

2. The instrument of claim 1, further comprising said actuating mechanism.

3. The instrument of claim 1, wherein said movement of said elongate element comprises pulling said elongate element.

4. The instrument of claim 1, said formation comprising a pair of jaws, wherein said at least one actuated body comprises a pair of actuator pins axially slidable to open and close said pair of jaws.

5. The instrument of claim 4, further comprising said actuating mechanism, wherein said actuating mechanism comprises at least one rotatable actuating body coupleable with said at least one actuated body, said at least one actuated body driveable by said rotatable actuating body when said actuated and actuating bodies are operably engaged.

6. The instrument of claim 5, said actuating mechanism further comprising a second rotatable actuating body for moving said shaft in a second degree of freedom.

7. The instrument of claim 6, said second degree of freedom comprising rotating said shaft about its longitudinal axis.

8. The instrument of claim 6, said second degree of freedom comprising moving said shaft axially along its longitudinal axis.

9. The instrument of claim 1, wherein said end effector comprises a scalpel.

10. A robotic surgical system, comprising:
    a robotic manipulator arm;
    a drive assembly disposed on the robotic manipulator arm, said drive assembly operatively coupled to a control unit operable by inputs from an operator;
    a surgical instrument removably coupleable to said drive assembly, said instrument having a proximal portion and a distal portion, said instrument including at least one distal end effector member, said proximal portion comprising a first plurality of movable bodies;
    said instrument comprising a plurality of joints, at least one of said joints being coupled to said end effector member, said joints being coupled to said first plurality of movable bodies by a plurality of drive members; and
    said drive assembly having a second plurality of movable bodies, said second plurality of movable bodies engageable with said first plurality of movable bodies such that the operator's inputs to the control unit cause the drive members to move, thereby producing a corresponding movement of at least one of said joints;
    wherein said robotic manipulator arm is part of a remote centering mechanism operable to pivot said shaft about a fixed insertion point.

11. A robotic surgical system, comprising:
    a robotic manipulator arm;
    a drive assembly comprising a plurality of links, joints and motors, said drive assembly operatively coupled to a control unit operable by inputs from an operator, said drive assembly disposed on said robotic manipulator arm;
    a surgical instrument removably coupleable to said drive assembly, said instrument having a proximal portion and a distal portion, said instrument including at least one distal end effector member, said proximal portion comprising a first plurality of movable bodies;

said instrument comprising a plurality of joints, at least one of said joints being coupled to said end effector member, said joints being coupled to said first plurality of movable bodies by a plurality of drive members;

said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;

wherein said robotic manipulator arm is part of a remote centering mechanism operable to pivot said shaft about a fixed insertion point.

12. A robotic surgical system, comprising:

a robotic manipulator arm;

a drive assembly comprising a plurality of linkages and motors, said drive assembly operatively coupled to a control unit comprising a computer, said control unit operable by inputs from an operator, said drive assembly disposed on said robotic manipulator arm;

a surgical instrument removably coupleable to said drive assembly, said instrument having a proximal portion having an interface and a distal portion, and the proximal portion comprising a first plurality of movable bodies;

said instrument including at least first and second distal end effector members, said first and second members coupled to corresponding first and second drive members;

said instrument further comprising a plurality of distal joints, at least one of said joints being coupled to said end effector members in such a manner that said end effector members are movable independently of each other as a result of movement of said drive members, each drive member being engaged to one of said first plurality of movable bodies;

said joints being coupled to said first plurality of movable bodies by a plurality of drive members;

said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;

wherein said robotic manipulator arm is part of a remote centering mechanism operable to pivot said shaft about a fixed insertion point.

13. A surgical instrument comprising:

a shaft having a distal portion and a proximal portion, said distal portion movable relative to said proximal portion in a first degree of freedom;

at least one elongate element connected to the distal portion to cause movement in said first degree of freedom in response to movement of said at least one elongate element, at least one actuated body disposed at the proximal portion of said shaft, said at least one actuated body comprising a first actuated body coupled to said at least one elongate element such that driving said first actuated body causes movement of said at least one elongate element;

said shaft detachably coupleable to an actuating mechanism for selectively driving said at least one actuated body, said actuating mechanism disposed on a robotic manipulator arm;

wherein said robotic manipulator arm is part of a remote centering mechanism operable to pivot said shaft about a fixed insertion point.

14. A robotic surgical system, comprising:

a robotic manipulator arm;

a drive assembly, said drive assembly operatively coupled to a control unit operable by inputs from an operator, said drive assembly disposed on said robotic manipulator arm;

a surgical instrument removably coupleable to said drive assembly, said instrument having a proximal portion and a distal portion, said proximal portion comprising a first plurality of movable bodies, said distal portion coupled to said first plurality of movable bodies by a plurality of drive members; and said drive assembly having a second plurality of movable bodies, said second plurality of movable bodies engageable with said first plurality of movable bodies such that the operator's inputs to the control unit cause the drive members to move, thereby producing a corresponding movement of said distal portion wherein said robotic manipulator arm is part of a remote centering mechanism operable to pivot said shaft about a fixed insertion point.

* * * * *